(12) United States Patent
Nagele (10) Patent No.: US 10,799,104 B2
(45) Date of Patent: Oct. 13, 2020

(54) LARYNGOSCOPE WITH SPREADABLE BLADES

(71) Applicant: NitroBiomedical LLC, Chicago, IL (US)

(72) Inventor: Peter Nagele, Chicago, IL (US)

(73) Assignee: NITROBIOMEDICAL LLC, Chicago, IL (US)

(*) Notice: Subject to any disclaimer, the term of this patent is extended or adjusted under 35 U.S.C. 154(b) by 87 days.

(21) Appl. No.: 16/217,485

(22) Filed: Dec. 12, 2018

(65) Prior Publication Data

US 2019/0175008 A1 Jun. 13, 2019

Related U.S. Application Data

(60) Provisional application No. 62/598,295, filed on Dec. 13, 2017.

(51) Int. Cl.
| | |
|---|---|
| *A61B 1/267* | (2006.01) |
| *A61B 1/32* | (2006.01) |
| *A61B 1/00* | (2006.01) |
| *A61B 1/04* | (2006.01) |

(52) U.S. Cl.
CPC .......... *A61B 1/267* (2013.01); *A61B 1/00183* (2013.01); *A61B 1/32* (2013.01); *A61B 1/04* (2013.01)

(58) Field of Classification Search
CPC .................................. A61B 1/267; A61B 1/32
USPC ................................................... 600/184–245
See application file for complete search history.

(56) References Cited

U.S. PATENT DOCUMENTS

7,153,260 B1 12/2006 Girgis

*Primary Examiner* — Ellen C Hammond
*Assistant Examiner* — Tara Rose E Carter (57) ABSTRACT

A spreadable laryngoscope for improving visualization of a larynx or back of a throat is described herein. The laryngoscope comprises a handle having a handle compartment, a fixed blade and a pivotable blade extending from the handle, and a spreading mechanism. In a normal or resting position, the pivotable blade lies parallel to and beside the fixed blade such that the fixed blade and the pivotable blade are side to side. To activate the spreading mechanism, a lever arm is depressed such that the lever arm is moved towards the handle, which causes a connecting arm to pivot about a pivot rod. This, in turn, causes a pivoting arm to move, which moves and pivots a blade bracket of the pivotable blade within the handle compartment. The pivotable blade pivots away from the fixed blade, thereby placing the blades in a spreaded position.

20 Claims, 9 Drawing Sheets

LARYNGOSCOPE WITH SPREADABLE BLADES

CROSS-REFERENCES TO RELATED APPLICATIONS

This application is a non-provisional, and claims benefit of U.S. Patent Application No. 62/598,295, filed Dec. 13, 2017, the specification(s) of which is/are incorporated herein in their entirety by reference

FIELD OF THE INVENTION

The present invention relates to laryngoscopes, in particular, to a laryngoscope having an active spreading mechanism to spread its blades.

BACKGROUND OF THE INVENTION

Figure 3:
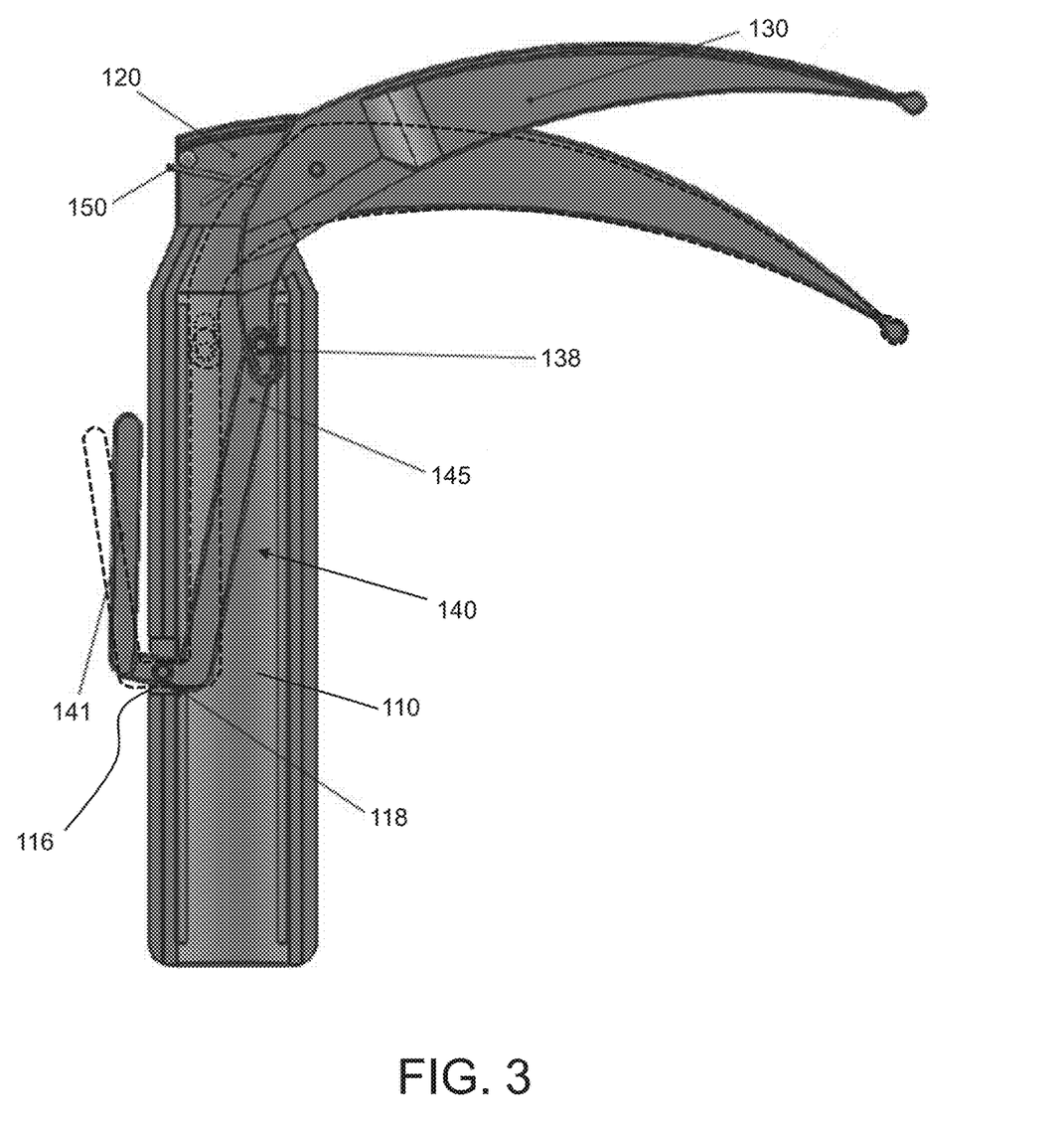
FIG. 3 shows a side view of the laryngoscope in a spreaded position. The broken-lines show a normal position relative to the spreaded configuration.

A laryngoscope is typically used to perform a visual examination of the back of the throat and larynx in order to diagnose causes of voice and breathing problems, swallowing issues, and throat or ear pain. Conventional laryngoscopes have a handle and a single straight or curved blade, such as the Miller or Macintosh blade, that is perpendicularly attached to the handle, thus forming an L-shape. Other conventional laryngoscopes may be straight, e.g., the handle and blade lie on the same plane. The laryngoscope may also have a light source at the tip of the blade to provide illumination. Further still, the laryngoscope may also have a camera mounted to the blade to provide a digital view of the larynx. As shown in FIG. 3, during a laryngoscopy procedure, a physician inserts the blade of the laryngoscope inside the patient's mouth and manipulates the tongue to view the back of the throat and larynx.

In addition to examination of the throat, the laryngoscope may be used to assist in the insertion of a tracheal tube for tracheal intubation in order to provide an airway during a general anesthesia, resuscitation, or surgical procedure. During an intubation procedure, the patient may be in supine position with the neck fully extended. The physician positions him or herself over the top of the patient's head so as to look down upon the patient's face. Using an L-shaped laryngoscope with a convex blade, the physician grips the handle and gently inserts the blade into the patient's mouth such that the tip of the blade is passed into the pharynx. The laryngoscope is moved upwardly such that the blade, being contoured to the curvature of the throat, lifts the tongue away from the pharynx and opens the epiglottis to expose the glottis, which is the opening to the larynx. Considerable skill and care is required in carrying out this procedure in order to avoid damage to the patient's teeth and soft tissue of the throat. By providing a clear passage to the patient's airway, an endotracheal intubation can then be manually inserted through the pharynx, and into the larynx and trachea.

However, since the pharynx and epiglottis vary in size and shape from patient to patient, creating a sufficient viewing passage with a laryngoscope that is improperly sized or improperly used can lead to throat injuries ranging from a sore throat to major damage of the larynx and/or pharynx. Thus, there is a need for a laryngoscope that can create a viewing passage without causing any injuries to the throat, or even to the teeth.

An example of a laryngoscope is taught in U.S. Pat. No. 7,153,260 of Girgis. Girgis discloses a laryngoscope that comprises a movable blade pivotally attached to the stationary blade and affixed to the movable handle for movement therewith so as to allow the movable blade to pivot away from the stationary blade when the movable handle is moved towards the stationary handle for spreading the posterior tissue defining the superior opening of the larynx away from the epiglottis as the tip disposed at the stationary blade depresses the epiglottis. The movable blade extends substantially over the stationary blade plus tip. However, since the movable blade lies directly over the stationary blade, when the movable blade is moved, the field of view would be obstructed by the movable blade.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

It is an objective of the present invention to provide a spreadable laryngoscope for improving visualization of a larynx or back of a throat. In some aspects, the laryngoscope may comprise a handle having a handle compartment, a fixed blade and a pivotable blade extending from the handle, and a spreading mechanism. The pivotable blade may be pivotably connected to the fixed blade via a pivot rod. In a normal or resting position, the pivotable blade lies parallel to and beside the fixed blade such that the fixed blade and the pivotable blade are side to side.

In one aspect, the spreading mechanism may comprise a lever arm extending from the handle and a pivoting arm disposed inside the handle compartment and operatively coupled to the lever arm and the pivotable blade. To activate the spreading mechanism, the lever arm is depressed such that the lever arm is moved towards the handle, which causes a connecting arm to pivot about a pivot rod. This, in turn, causes the pivoting arm to move, which moves and pivots a blade bracket of the pivotable blade within the handle compartment. The pivotable blade pivots away from the fixed blade, thereby placing the blades in a spreaded position.

As previously described, a conventional laryngoscope basically functions as an L-shaped tool that is lifted and has no moving parts or spreading mechanism. The laryngoscope of the present device features a built-in spreading mechanism that allows for an active spreading of the blades. For example, the lever arm is activated by being pressed down, which in turn, initiates a series of movements and pivots that substantially lift the pivotable blade. One of the unique and inventive technical features of the present invention is that the pivotable blade lies to the side of a fixed blade. Without wishing to limit the invention to any theory or mechanism, it is believed that the technical feature of the present invention advantageously provides for better field of view to visualize the larynx and the back of the throat. Another unique and inventive technical feature of the present invention is that the pivoting arm is disposed inside the handle. Without wishing to limit the invention to any theory or mechanism, it is believed that the technical feature of the present invention advantageously provides for a more sanitary and compact laryngoscope where the pivoting arm would not be pose as an obstruction to the laryngoscope procedure. None of the presently known prior references or work has the unique inventive technical feature of the present invention.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which.

DESCRIPTION OF PREFERRED EMBODIMENTS

Following is a list of elements corresponding to a particular element referred to herein:

100 laryngoscope
105 handle
110 handle compartment
111 proximal end of the handle
112 distal end of the handle
114 handle wall
116 handle wall aperture
118 first pivot rod
120 fixed blade
122 proximal end of the fixed blade
124 distal end of the fixed blade
128 second pivot rod
130 pivotable blade
132 proximal end of the pivotable blade
134 distal end of the pivotable blade
135 blade bracket
140 spreading mechanism
141 lever arm
142 proximal end of the lever arm
143 distal end of the lever arm
144 connecting arm
145 pivoting arm
146 proximal end of the pivoting arm
147 distal end of the pivoting arm
148 third pivot rod
149 resistance spring
150 end of the resistance spring
151 spring rod
152 resistance rod Referring now to FIGS. 1-15, the present invention features a spreadable laryngoscope (100) for improving visualization of a larynx or back of a throat. According to some embodiments, the laryngoscope (100) may comprise a handle (105), a fixed blade (120) and a pivotable blade (130) extending from the handle (105), and a spreading mechanism (140).

Figure 2:
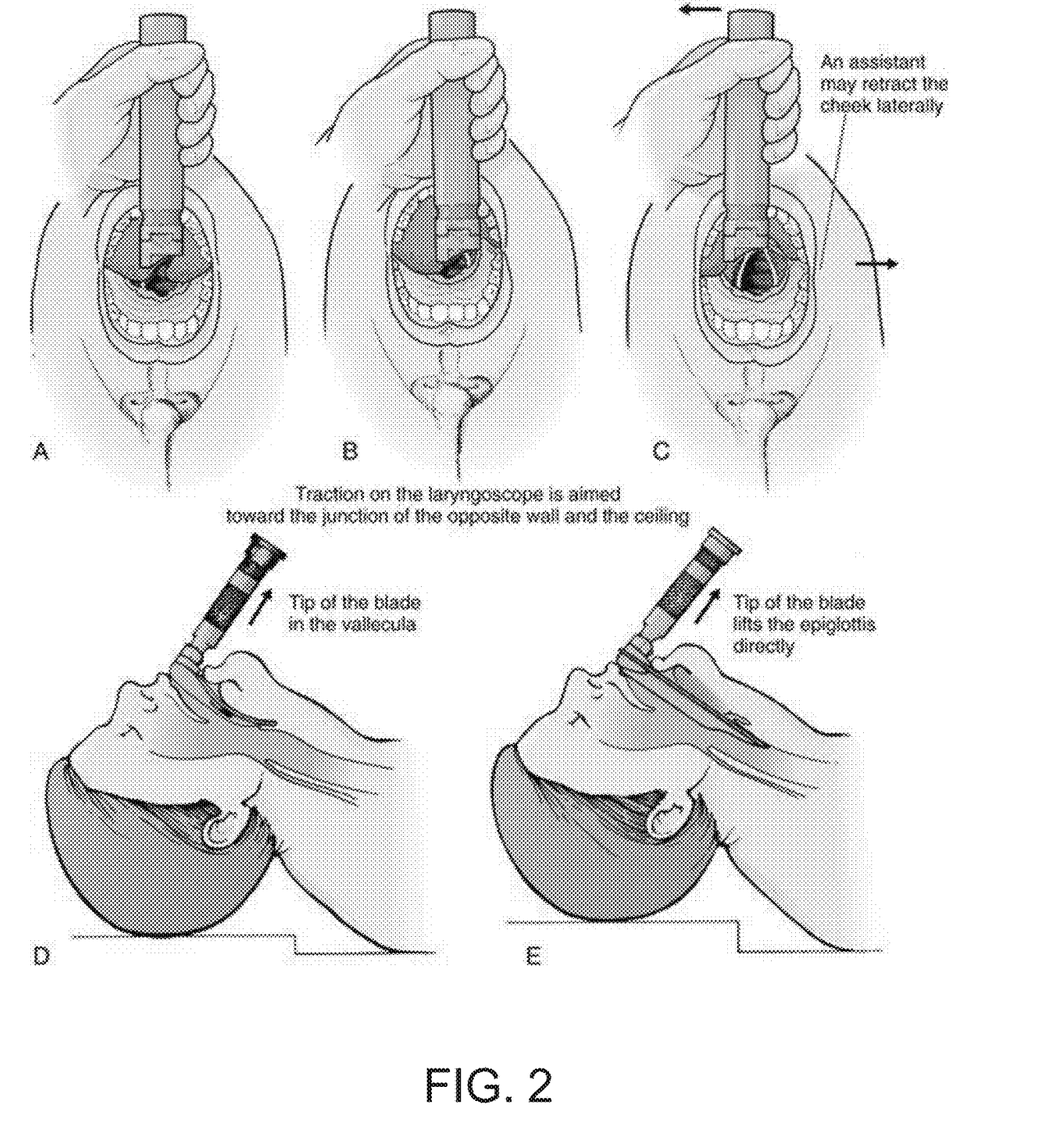
FIG. 2 illustrates an example of a laryngoscopy procedure using conventional laryngoscopes.

In some embodiments, the handle comprises a handle compartment (110) disposed therein, a handle wall (114), an aperture (116) disposed through the handle wall, and a first pivot rod (118) horizontally disposed in the aperture (116) and connected to the handle wall (114). As shown in FIG. 2, the aperture (116) may be located on an opposite side of the handle wall (114) relative to the direction of the blades. The first pivot rod (118) is disposed across the aperture and attached to the handle wall (114).

Figure 7A:
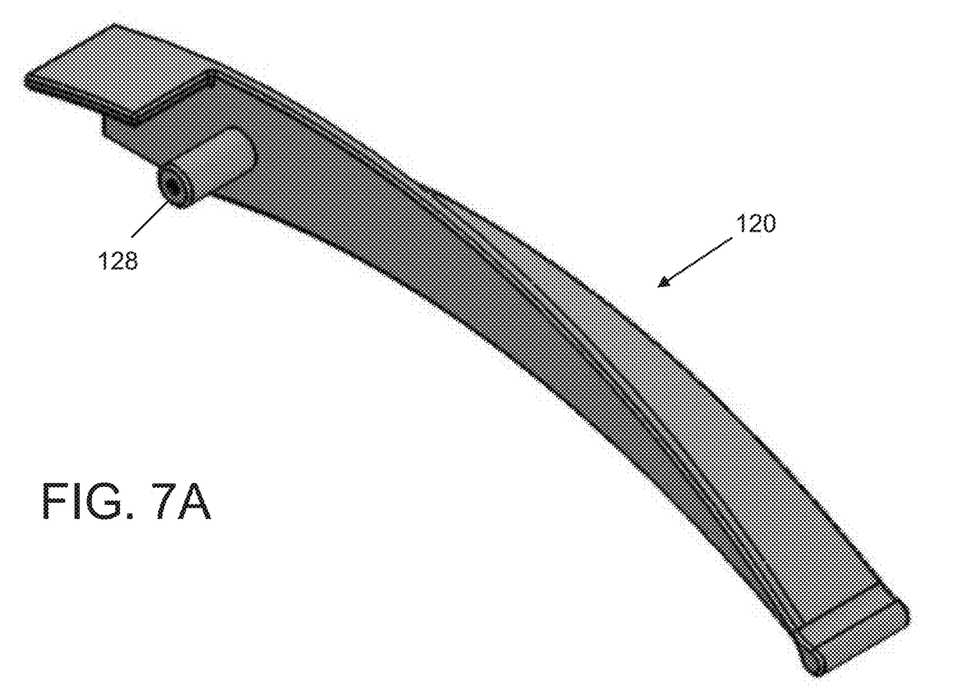
FIG. 7A shows a perspective view of a stationary blade of the laryngoscope.
Figure 8A:
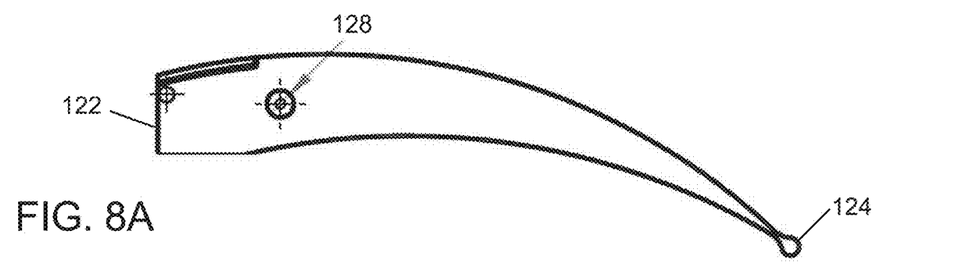
FIG. 8A shows a side view of the stationary blade.
Figure 9A:
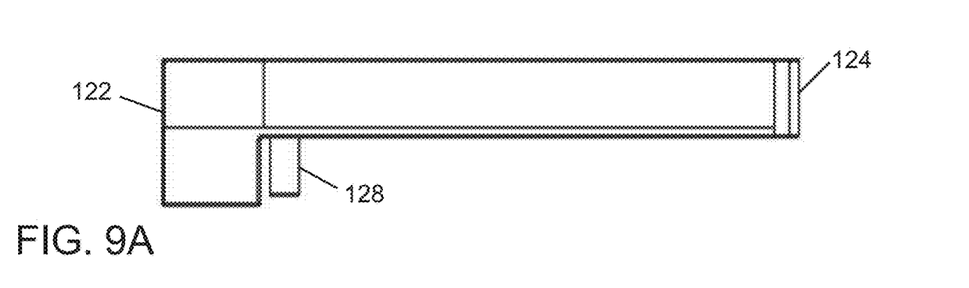
FIG. 9A shows a top view of the stationary blade.
Figure 10A:
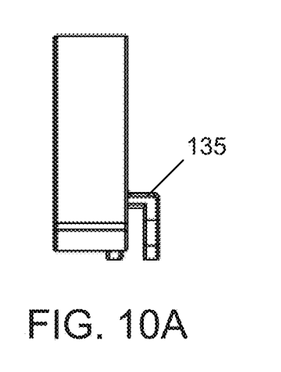
FIG. 10A shows a front view of the pivotable blade.

In some embodiments, a proximal end (122) of the fixed blade is fixedly attached to a proximal end (111) of the handle. As shown in FIG. 7A, the fixed blade may have a flat bottom surface and a side surface perpendicularly and upwardly extending from the bottom surface, as shown in FIGS. 8A, 9A, and 10A. The side surface may also taper from the proximal end (122) to the distal end (124) of the fixed blade. Further still, the side surface may be directly adjacent to the pivotable blade (130).

In some embodiments, the distal end (124) of the fixed blade has a rounded tip. In other embodiments, a second pivot rod (128) may be fixedly attached to the fixed blade (120) near its proximal end (122) and disposed through the pivotable blade (130) near its proximal end (132). In further embodiments, a resistance rod (152), located at the proximal end (122), may project from the fixed blade (120) towards the pivotable blade.

Figure 4:
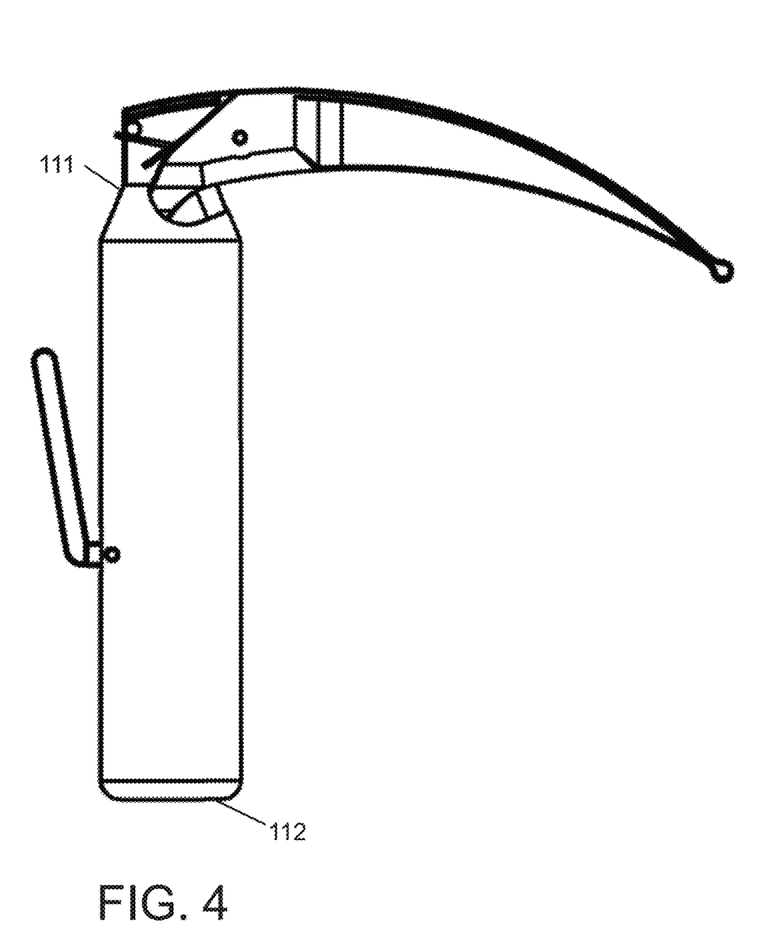
FIG. 4 shows another side view of the laryngoscope in a normal position.
Figure 5:
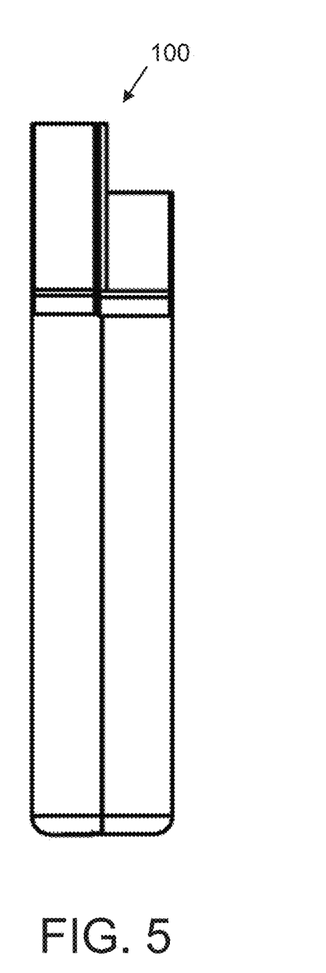
FIG. 5 shows a front view of the laryngoscope.
Figure 6:
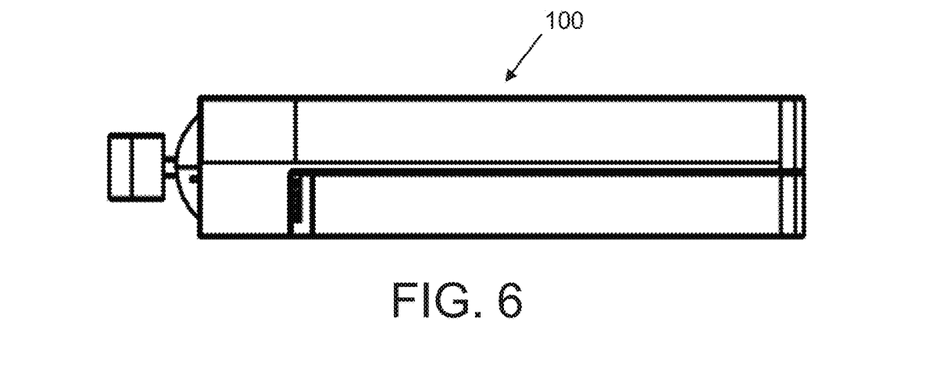
FIG. 6 shows a top view of the laryngoscope.
Figure 8B:
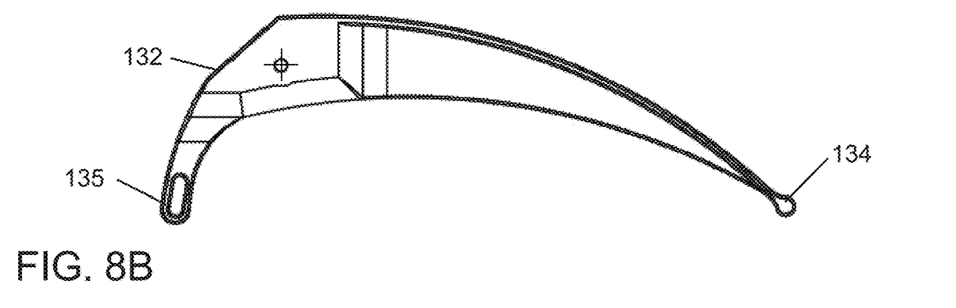
FIG. 8B shows a side view of the pivotable blade.
Figure 9B:
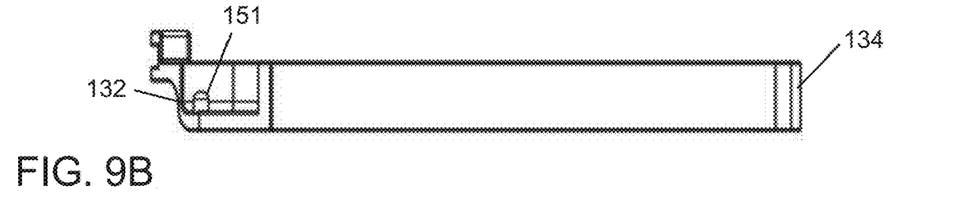
FIG. 9B shows a top view of the pivotable blade.
Figure 10B:
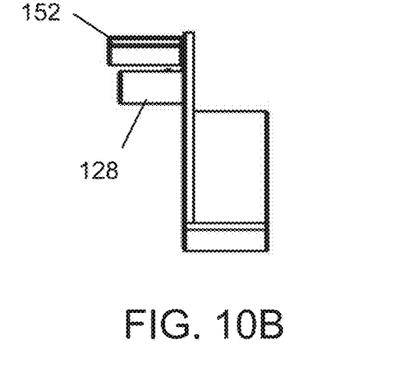
FIG. 10B shows a front view of the stationary blade.
Figure 11A:
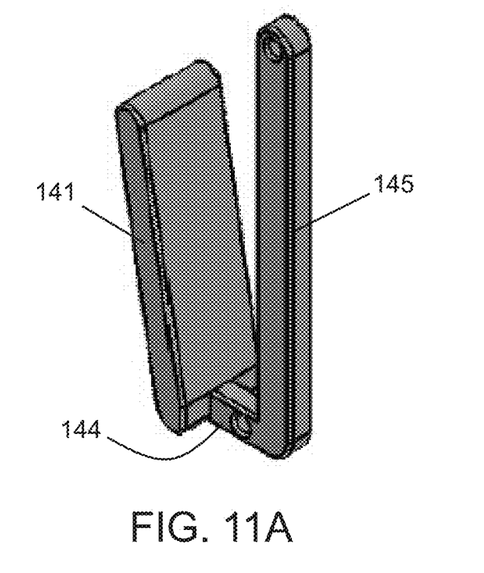
FIG. 11A shows a lever arm and a pivoting arm of a spreading mechanism of the laryngoscope.
Figure 11B:
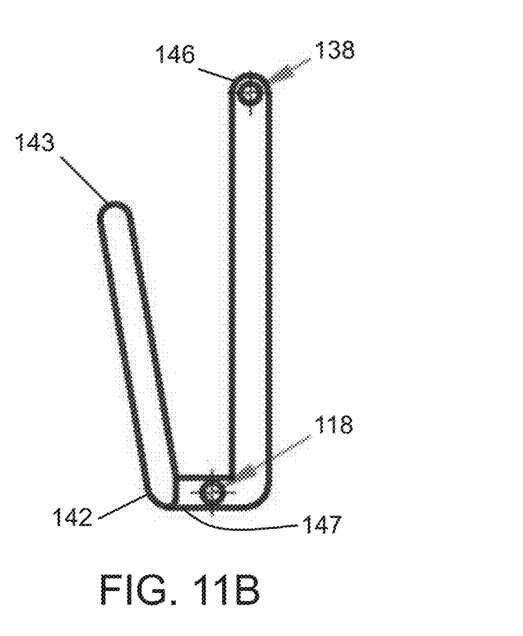
FIG. 11B shows a side view of the lever arm and the pivoting arm.
Figure 12A:
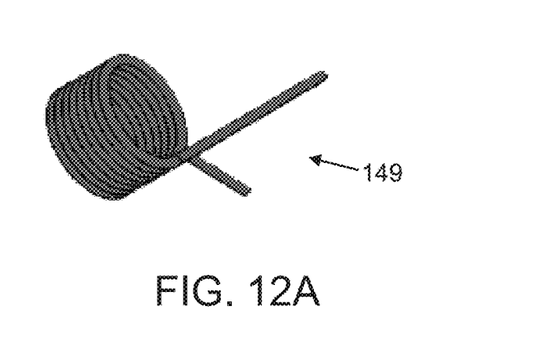
FIG. 12A shows an embodiment of a spring of the spreading mechanism.
Figure 12B:
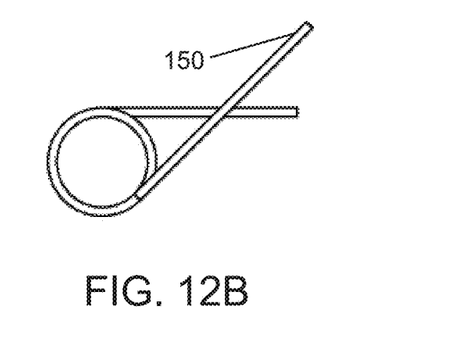
FIG. 12B shows a side view of the spring.
Figure 13:
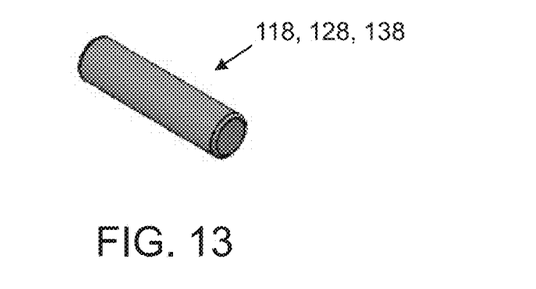
FIG. 13 shows an embodiment of a pivot rod of the spreading mechanism.
Figure 14A:
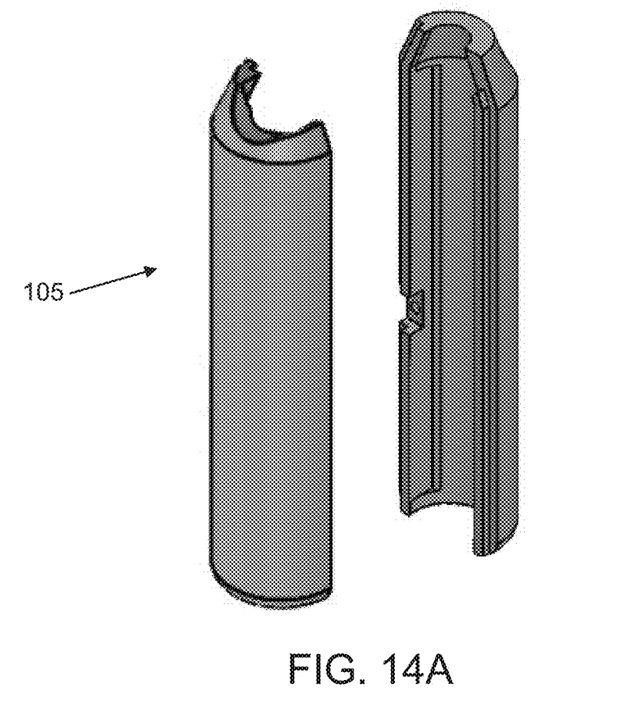
FIG. 14A shows an exploded view of the handle of the laryngoscope.
Figure 14B:
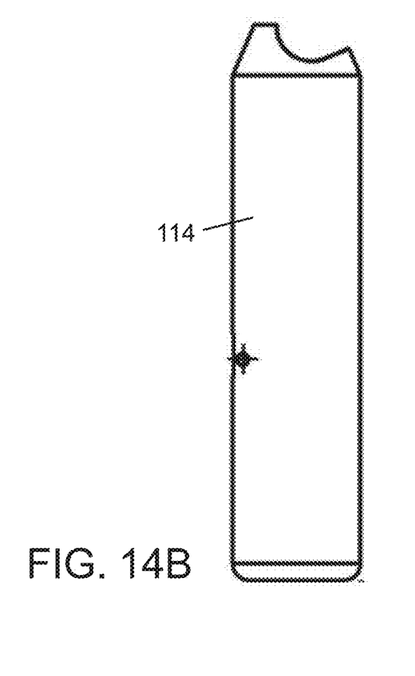
FIG. 14B shows an exterior side view of the handle.
Figure 14C:
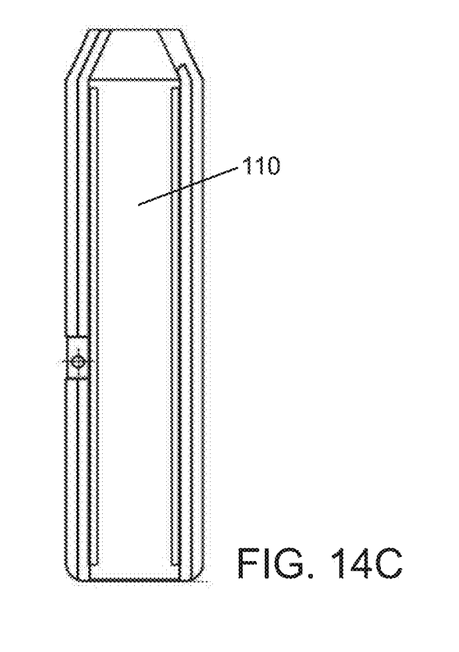
FIG. 14C shows an interior side view of the handle.

In some embodiments, the pivotable blade (130) may be pivotably connected to the fixed blade (120) via the second pivot rod (128). In a normal or resting position, as show in FIG. 4, the pivotable blade (130) lies parallel to and beside the fixed blade (120) such that the fixed blade and the pivotable blade are side to side, as show in FIGS. 5-6. In some embodiments, the pivotable blade (130) may have a flat top surface and a side surface perpendicularly and downwardly extending from the top surface, as shown in FIGS. 8B, 9B, and 10B. The side surface may also taper from the proximal end (132) to the distal end (134) of the pivotable blade. Further still, the side surface of the pivotable blade (130) may be directly adjacent to the side surface of the fixed blade and the edges of the side surfaces are aligned, as shown in FIGS. 4-5.

In some embodiments, the distal end (134) of the pivotable blade has a rounded tip. In other embodiments, a blade bracket (135) extends from the proximal end (132) of the pivotable blade (130) and is disposed inside the handle compartment (110). In further embodiments, a spring rod (151) projects from the pivotable blade (130) near its proximal end (132) and is biased towards the fixed blade (120).

As used herein, the phrase "pivotably connected" refers to coupling where a pivot rod is disposed through a component that allows for said component to pivot, or rotate, about said pivot rod.

According to one embodiment, the spreading mechanism (140) may comprise a lever arm (141) extending from the handle (105), a pivoting arm (145) disposed inside the handle compartment (110), and a resistance spring (149) operatively coupled to the pivotable blade. The pivoting arm (145) may be operatively coupled to the lever arm (141) via a connecting arm (144). In some embodiments, the connecting arm (144) may be disposed through the aperture (116) of the handle wall and pivotably connected to the first pivot rod (118). In other embodiments, a proximal end (146) of the pivoting arm may be pivotably connected to the blade bracket (135) of the pivotable blade via a third pivot rod (148) such that the pivoting arm (145) is operatively coupled to the pivotable blade (130).

In further embodiments, the resistance spring (149) is juxtaposed between the fixed blade (120) and the pivotable blade (130), and the spring rod (151) is disposed through the resistance spring (149). The resistance spring (149) may be configured to maintain the normal position of the blades (120, 130) such that the pivotable blade (130) lies parallel to and beside the fixed blade (120), as shown in FIG. 4. In still further embodiments, an end (150) of the resistance spring can rest against the resistance rod (152) of the fixed blade (120).

To activate the spreading mechanism, the lever arm (141) is depressed such that the lever arm is moved towards the the handle wall, which causes the connecting arm (144) to pivot about the first pivot rod (118). This, in turn, causes the pivoting arm (145) to move, which moves the blade bracket (135) within the handle compartment (110). The blade bracket (135) also pivots about the third pivot rod (148), and the pivotable blade (130) pivots about the second pivot rod (128) and away from the fixed blade (120). The distal end (134) of the pivotable blade (130) moves away from a distal end (124) of the fixed blade, thereby placing the blades (120, 130) in a spreaded position. In preferred embodiments, the resistance rod (152) can provide resistance against the resistance spring (149) when the blades (120, 130) are in the normal position, and when tension is applied to the resistance spring when the blades (120, 130) are in the spreaded position.

According to another embodiment, the spreading mechanism (140) may comprise the lever arm (141) extending from the handle (105), and the pivoting arm (145) operatively coupled to the lever arm (141). For example, a proximal end (142) of the lever arm (141) may be connected to a distal end (147) of the pivoting arm. The distal end (147) of the pivoting arm is disposed through the aperture (116) of the handle wall and pivotably connected to the first pivot rod (118). A portion of the pivoting arm from where it is connected to the first pivot rod (118) to its proximal end (146) is disposed inside the handle compartment (110). The pivoting arm (145) may be operatively coupled to the pivotable blade (130). For instance, the proximal end (146) of the pivoting arm is pivotably connected to the blade bracket (135) of the pivotable blade via a third pivot rod (148) that is disposed inside the handle compartment (110).

Similarly, to activate the spreading mechanism, the lever arm (141) is depressed, which causes the distal end (147) of the pivoting arm to pivot about the first pivot rod (118). This, in turn, causes the pivoting arm (145) to move, which causes the blade bracket (135) to move and pivot about the third pivot rod (148). The pivotable blade (130) then pivots about the second pivot rod (128) and away from the fixed blade (120) such that a distal end (134) of the pivotable blade (130) moves away from a distal end (124) of the fixed blade, thereby displacing the blades (120, 130) from the normal position into the spreaded position.

In other embodiments, the spreading mechanism (140) may further comprise a resistance spring (149) operatively couple to the pivotable blade. The resistance spring (149) may be juxtaposed between the fixed blade (120) and the pivotable blade (130), and the spring rod (151) may be disposed through the resistance spring (149). The resistance spring (149) is configured to maintain the normal position of the blades (120, 130) by resting an end (150) of the resistance spring against the resistance rod (152). In some embodiments, the resistance rod (152) can provide resistance to the resistance spring (149) when the blades (120, 130) are in the normal position, and when tension is applied to the resistance spring when the blades (120, 130) are in the spreaded position.

Figure 7B:
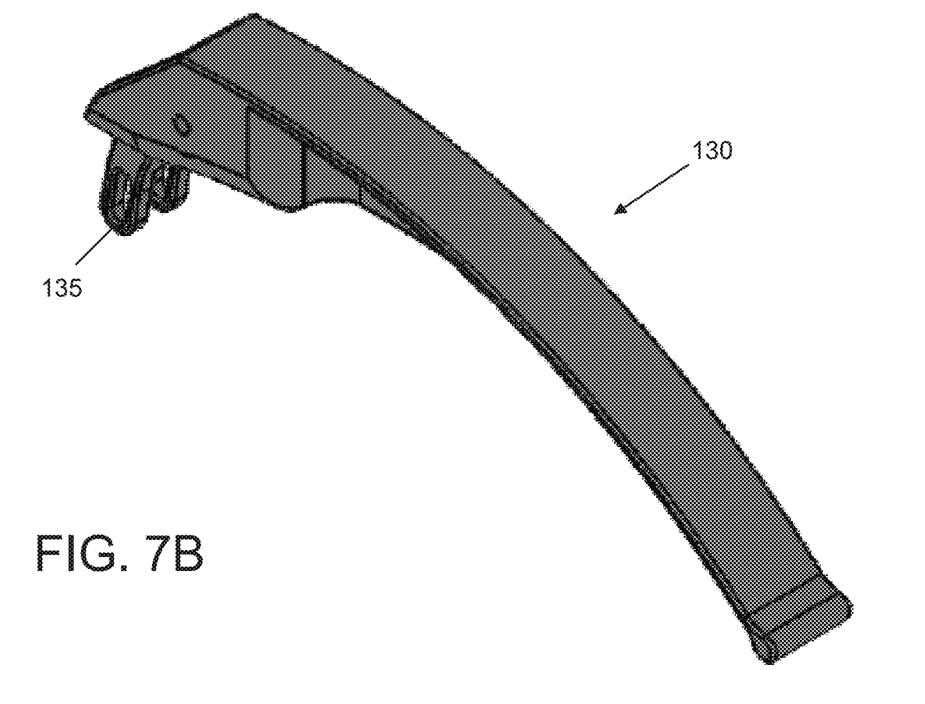
FIG. 7B shows a perspective view of a pivotable blade of the laryngoscope.

In some embodiments, the blade bracket (135) may comprise two parallel bars, as shown in FIGS. 7B and 10A. In some embodiments, the proximal end (146) of the pivoting arm may be juxtaposed between the two bars of the blade bracket and the third pivot rod (148) is disposed therethrough.

In one embodiment, as shown in FIG. 3, a distal end (143) of the lever arm is biased towards the proximal end (111) of the handle. In an alternative embodiment, the distal end (143) of the lever arm is biased towards a distal end (112) of the handle (not shown). It is desired that the lever arm be oriented in any suitable manner that provides a lever action to activate the spreading mechanism. Further still, it is desired that the lever arm be positioned on the handle at a location that is ergonomical to the user. For example, the lever arm (141) and the blades (120, 130) may extend from the handle (105) in opposing directions. Also, the lever arm (141) maybe positioned around the middle of the handle or, alternatively, closer to the distal end of the handle.

In alternative embodiments, the lever arm may be replaced with a push button that can activate the spreading mechanism. For example, the push button may be operatively connected to the pivoting arm. In some embodiments, the push button may be located on the handle wall or, alternatively, on the distal end of the handle.

In some embodiments, the handle (105) may have a length ranging from about 5 to 10 inches. For example, the handle (105) may be about 6 inches. In other embodiments, the length of the lever arm may be about 2 to 3 inches. In still other embodiments, the length of the blades may be about 3 to 6 inches. One of ordinary skill in the art would appreciate that an appropriate length of the blades is selected for a specific patent, and would vary from patient to patient. For instance, one would select shorter blades, such as 3" blades, for children, and longer blades, such as 5" blades, for adults. Preferably, the handle can accommodate different lengths of blades so that the blades can be interchangeable.

In some embodiments, the laryngoscope (100) may be constructed from a medical-grade metal, such as stainless steel. In other embodiments, the laryngoscope (100) may be constructed from a medical-grade, rigid plastic. In further embodiments, the laryngoscope (100) may be a combination of materials. For example, the handle and spreading mechanism may be constructed from medical-grade metal to allow for re-use, and the blades may be constructed from plastic so that blades are disposable.

Figure 1:
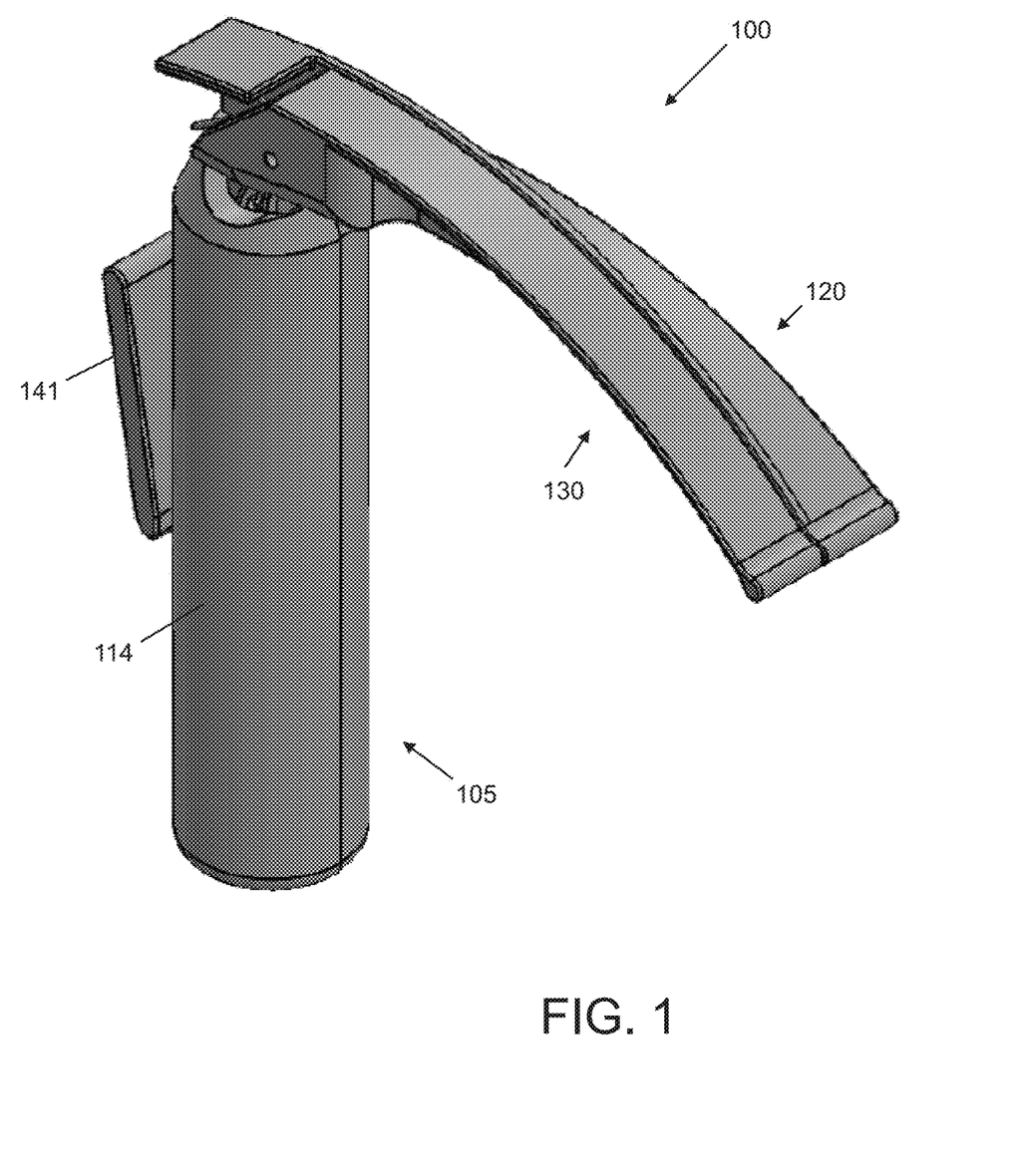
FIG. 1 shows a perspective view of a laryngoscope of the present invention.

In one embodiment, the blades (120, 130) are curved towards the distal end (112) of the handle, as shown in FIG. 1. In another embodiment, the blades (120, 130) are relatively straight.

In further embodiments, the spreadable laryngoscope (100) described herein may be used in a method for improving visualization of the larynx or back of the throat of a patient during a laryngoscopy procedure. According to some embodiments, the method may comprise providing the laryngoscope (100), inserting the blades (120, 130) through a mouth of the patient while grasping the handle (105) such that the distal ends of the blades are positioned in the back of the throat, moving the handle (105) so that the blades (120, 130) press against a tongue and move the tongue away from a pharynx to open an epiglottis and expose the glottis to a field of view, and depressing the lever arm (141) to activate the spreading mechanism that causes the pivotable blade (130) to pivot away from the fixed blade (120), thereby displacing the blades (120, 130) from the normal position into a spreaded position, thus increasing the field of view.

Figure 15:
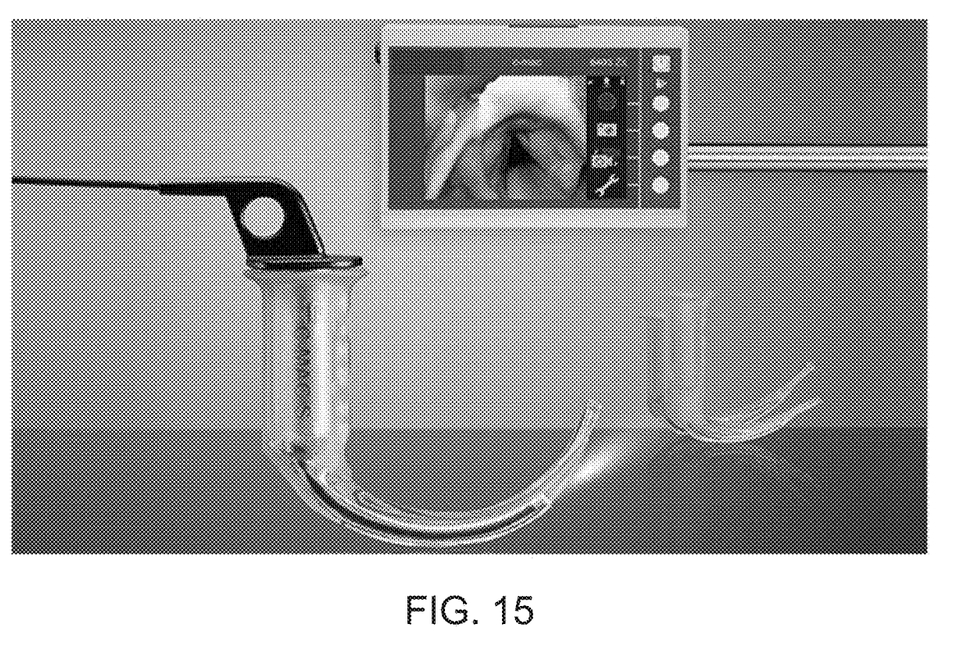
FIG. 15 shows an embodiment of the laryngoscope operatively coupled to a imaging system for digitally viewing the back of the throat.

In still further embodiments, the spreadable laryngoscope (100) of the present invention may be operatively coupled to an imaging system, as shown in FIG. 15. In some embodiments, the imaging system may comprise a camera or image sensor and a light source. The camera or image sensor and light source may be mounted onto one of the blades of the laryngoscope. For example, the camera or image sensor and light source may be mounted onto the fixed blade (120). In some embodiments, the camera or image sensor can capture digital images or stream video of the back of the throat and larynx. The captured images or video stream may then be displayed on a user interface, such as a digital screen. In other embodiments, the light source can illuminate the area of interest without obstructing or interfering with the camera or image sensor.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A spreadable laryngoscope (100) for improving visualization of a larynx or back of a throat, said laryngoscope (100) comprising:
   a. a handle (105) having a handle compartment (110) disposed therein, a handle wall (114), an aperture (116) disposed through the handle wall, and a first pivot rod (118) horizontally disposed in the aperture (116) and connected to the handle wall (114);
   b. a fixed blade (120) extending from the handle (105), wherein a proximal end (122) of the fixed blade is fixedly attached to a proximal end (111) of the handle;
   c. a pivotable blade (130) extending from the handle (105) and pivotably connected to the fixed blade (120) via a second pivot rod (128), wherein the pivotable blade (130) normally lies parallel to and beside the fixed blade (120) such that the fixed blade and the pivotable blade are side to side, wherein a blade bracket (135) extends from a proximal end (132) of the pivotable blade (130) and is disposed inside the handle compartment (110); and
   d. a spreading mechanism (140) comprising:
      i. a lever arm (141) extending from the handle (105);
      ii. a pivoting arm (145) disposed inside the handle compartment (110), wherein the pivoting arm (145) is operatively coupled to the lever arm (141) via a connecting arm (144) and operatively coupled to the pivotable blade (130), wherein the connecting arm (144) is disposed through the aperture (116) of the handle wall and pivotably connected to the first pivot rod (118), wherein a proximal end (146) of the pivoting arm is pivotably connected to the blade bracket (135) of the pivotable blade via a third pivot rod (148); and
      iii. a resistance spring (149) operatively couple to the pivotable blade;
   wherein the resistance spring (149) maintains a normal position of the blades (120, 130) such that the pivotable blade (130) lies parallel to and beside the fixed blade (120),
   wherein when the lever arm (141) is depressed, the connecting arm (144) pivots about the first pivot rod (118), the pivoting arm (145) is moved, the blade bracket (135) is moved within the handle compartment (110) and pivots about the third pivot rod (148), and the pivotable blade (130) pivots about the second pivot rod (128) and away from the fixed blade (120) such that a distal end (134) of the pivotable blade (130) moves away from a distal end (124) of the fixed blade, thereby placing the blades (120, 130) in a spreaded position.

2. The laryngoscope (100) of claim 1, wherein the resistance spring (149) is juxtaposed between the fixed blade (120) and the pivotable blade (130).

3. The laryngoscope (100) of claim 2, wherein a spring rod (151) projects from the pivotable blade (130) near its proximal end (132) and is disposed through the resistance spring (149).

4. The laryngoscope (100) of claim 3, wherein an end (150) of the resistance spring rests against a resistance rod (152) that projects from the proximal end (122) of the fixed blade (120) towards the pivotable blade (130).

5. The laryngoscope (100) of claim 4, wherein the resistance rod (152) provides resistance against the resistance spring (149) when the blades (120, 130) are in the normal position and when tension is applied to the resistance spring when the blades (120, 130) are in the spreaded position.

6. A spreadable laryngoscope (100) for improving visualization of a larynx or back of a throat, said laryngoscope (100) comprising:
   a. a handle (105) having a handle compartment (110) disposed therein, a handle wall (114), an aperture (116) disposed through the handle wall, and a first pivot rod (118) horizontally disposed in the aperture (116) and connected to the handle wall (114);
   b. a fixed blade (120) extending from the handle (105), wherein a proximal end (122) of the fixed blade is fixedly attached to a proximal end (111) of the handle;
   c. a pivotable blade (130) extending from the handle (105) and pivotably connected to the fixed blade (120) via a second pivot rod (128), wherein when in a normal position, the pivotable blade (130) lies parallel to and beside the fixed blade (120) such that the fixed blade and the pivotable blade are side to side, wherein a blade bracket (135) extends from a proximal end (132) of the pivotable blade (130) and is disposed inside the handle compartment (110); and
   d. a spreading mechanism (140) comprising:
      i. a lever arm (141) extending from the handle (105); and
      ii. a pivoting arm (145) operatively coupled to the lever arm (141) and operatively coupled to the pivotable blade (130), wherein a distal end (147) of the pivoting arm is disposed through the aperture (116) of the handle wall and pivotably connected to the first pivot rod (118), wherein a proximal end (142) of the lever arm (141) is connected to the distal end (147) of the pivoting arm, wherein a proximal end (146) of the pivoting arm is pivotably connected to the blade bracket (135) of the pivotable blade via a third pivot rod (148) disposed inside the handle compartment (110), wherein a portion of the pivoting arm from the first pivot rod (118) to the proximal end (146) is disposed inside the handle compartment (110);
   wherein when the lever arm (141) is depressed, the distal end (147) of the pivoting arm pivots about the first pivot rod (118), the pivoting arm (145) is moved, the blade bracket (135) is moved and pivots about the third pivot rod (148), and the pivotable blade (130) pivots about the second pivot rod (128) and away from the fixed blade (120) such that a distal end (134) of the pivotable blade (130) moves away from a distal end (124) of the fixed blade, thereby displacing the blades (120, 130) from the normal position into a spreaded position.

7. The laryngoscope (100) of claim 6, wherein the spreading mechanism (140) further comprises a resistance spring (149) operatively couple to the pivotable blade, wherein the resistance spring (149) maintains the normal position of the blades (120, 130) such that the pivotable blade (130) lies parallel to and beside the fixed blade (120).

8. The laryngoscope (100) of claim 7, wherein the resistance spring (149) is juxtaposed between the fixed blade (120) and the pivotable blade (130).

9. The laryngoscope (100) of claim 8, wherein a spring rod (151) projects from the pivotable blade (130) near its proximal end (132) and is disposed through the resistance spring (149).

10. The laryngoscope (100) of claim 9, wherein an end (150) of the resistance spring rests against a resistance rod (152) that projects from the proximal end (122) of the fixed blade (120) towards the pivotable blade (130).

11. The laryngoscope (100) of claim 10, wherein the resistance rod (152) provides resistance to the resistance spring (149) when the blades (120, 130) are in the normal position and when tension is applied to the resistance spring when the blades (120, 130) are in the spreaded position.

12. The laryngoscope (100) of claim 6, wherein the second pivot rod (128) is fixedly attached to the fixed blade (120) near its proximal end (122) and disposed through the pivotable blade (130) near its proximal end (132).

13. The laryngoscope (100) of claim 6, wherein the blade bracket (135) comprises two parallel bars, wherein the proximal end (146) of the pivoting arm is juxtaposed between the two bars of the blade bracket and the third pivot rod (148) is disposed therethrough.

14. The laryngoscope (100) of claim 6, wherein a distal end (143) of the lever arm is biased towards the proximal end (111) of the handle.

15. The laryngoscope (100) of claim 6, wherein a distal end (143) of the lever arm is biased towards a distal end (112) of the handle.

16. The laryngoscope (100) of claim 6, wherein the blades (120, 130) and the lever arm (141) extend from the handle (105) in opposing directions.

17. The laryngoscope (100) of claim 6, wherein the laryngoscope (100) is constructed from a medical-grade metal.

18. The laryngoscope (100) of claim 17, wherein the medical-grade metal is stainless steel.

19. The laryngoscope (100) of claim 6, wherein the laryngoscope (100) is constructed from a medical-grade, rigid plastic.

20. The laryngoscope (100) of claim 6, wherein the blades (120, 130) are straight.

* * * * *